United States Patent
Flachsmann et al.

(10) Patent No.: US 7,655,701 B2
(45) Date of Patent: Feb. 2, 2010

(54) CYCLOALKYLIDENE-(ORTHO SUBSTITUTED PHENYL)-ACETONITRILES AND THEIR USE AS ODORANTS

(75) Inventors: Felix Flachsmann, Duebendorf (CH); Jean-Pierre Bachmann, Wadenswil (CH)

(73) Assignee: Givaudan SA, Vernier (CH)

( * ) Notice: Subject to any disclaimer, the term of this patent is extended or adjusted under 35 U.S.C. 154(b) by 228 days.

(21) Appl. No.: 11/917,250

(22) PCT Filed: Jun. 15, 2006

(86) PCT No.: PCT/CH2006/000322

§ 371 (c)(1),
(2), (4) Date: Dec. 12, 2007

(87) PCT Pub. No.: WO2006/133592

PCT Pub. Date: Dec. 21, 2006

(65) Prior Publication Data

US 2008/0200554 A1    Aug. 21, 2008

(30) Foreign Application Priority Data

Jun. 16, 2005   (GB) .................. 0512284.1

(51) Int. Cl.
*A61K 8/40*     (2006.01)
*C07C 255/33*   (2006.01)
*C11D 3/50*     (2006.01)

(52) U.S. Cl. .......... 514/649; 510/106; 512/6; 558/388; 558/410

(58) Field of Classification Search ........ None
See application file for complete search history.

(56) References Cited

U.S. PATENT DOCUMENTS 2,762,812 A    9/1956    Archer et al.
3,408,396 A    10/1968   Suh et al.

OTHER PUBLICATIONS

Acta Pharmaceutica Jugoslavica vol. 31, No. 3, 1981. pp. 143-150 Stjepan Mutak et al., "Synthesis and pharmacological activity of 2-aryl-2-(1-cyclohexenyl)-butylamine derivatives".
Great Britain search report, Sep. 14, 2005.

*Primary Examiner*—Kamal A Saeed
(74) *Attorney, Agent, or Firm*—Norris McLaughlin & Marcus, PA

(57) ABSTRACT

Compounds of formula (I) and their use as fragrance ingredients

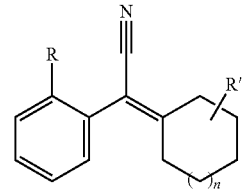

wherein
R is selected from methyl, ethyl, propyl, isopropyl, methoxy and ethoxy;
R is hydrogen or methyl; and
n is 0 or 1.

14 Claims, No Drawings

CYCLOALKYLIDENE-(ORTHO SUBSTITUTED PHENYL)-ACETONITRILES AND THEIR USE AS ODORANTS

This is an application filed under 35 USC 371 of PCT/CH2006/000322.

The present invention refers to novel cycloalkylidene-(ortho substituted phenyl)-acetonitriles, and their use as odorants. This invention relates furthermore to a method of their production and fragrance compositions comprising them.

In the fragrance industry there is a constant demand for new compounds that enhance or improve on odour notes, or impart new odour notes. In particular powerful, relative non-volatile compounds are of interest which makes them very attractive as long-lasting odour notes, especially for the use in fabric care products.

It was found that certain cycloalkylidene-(ortho substituted phenyl)-acetonitriles possess a remarkable low odor threshold value compared to their un-substituted analogues, such as cyclohexylidene-phenyl-acetonitrile, also known under the trade name Peonile®.

As used herein, "odor threshold value" means the lowest concentration of a vapour in the air which can be detected by smell. Generally speaking, it can be said that a compound with a low odor threshold value is more powerful than a compound with a high odor threshold value and thus allows the use of very low concentration in a fragrance composition to achieve an olfactory effect.

The present invention refers in one of its aspects to compounds of formula (I)

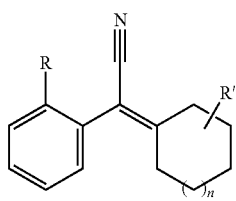

(I)

wherein
R is selected from methyl, ethyl, propyl, isopropyl, methoxy and ethoxy;
R' is hydrogen or methyl; and
n is 0 or 1.

The compounds of formula (I) wherein R' is methyl comprise one chiral centre and as such may exist as a mixture of stereoisomers, or they may be resolved as isomerically pure forms. Furthermore, hindered rotation around the aryl-acetonitrile single bond of the compounds of formula (I) leads to the formation of atropisomers, which at room temperature might be sufficiently stable to exhibit distinguishable olfactory properties. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization, resolution of mixtures of stereoisomers via chemical methods or stereoselective synthesis.

Particular preferred compounds of formula (I) are cyclohexylidene-o-tolyl-acetonitrile, cyclopentylidene-o-tolyl-acetonitrile, cyclohexylidene-(2-methoxy-phenyl)-acetonitrile, and 2-(2-methylcyclohexylidene)-2-o-tolylacetonitrile.

The compounds according to the present invention may be used alone or in combination with known odorant molecules selected from the extensive range of natural and synthetic molecules currently available, such as ethereal oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The following list comprises examples of known odorant molecules, which may be combined with the compounds of the present invention:

ethereal oils and extracts, e.g. oak moss absolute, basil oil, tropical fruit oils, such as bergamot oil and mandarine oil, mastic absolute, myrtle oil, palmarosa oil, patchouli oil, petitgrain oil, wormwood oil, lavender oil, rose oil, jasmin oil, ylang-ylang oil and sandalwood oil.

alcohols, e.g. cis-3-hexenol, cinnamic alcohol, citronellol, Ebanol™, eugenol, farnesol, geraniol, menthol, nerol, rhodinol, Super Muguet™, linalool, phenylethyl alcohol, Sandalore™, terpineol and Timberol™ (1-(2,2,6-Trimethylcyclohexyl)hexan-3-ol).

aldehydes and ketones, e.g. citral, hydroxycitronellal, Lilial®, methylnonylacetaldehyde, anisaldehyde, allylionone, verbenone, nootkatone, geranylacetone, α-amylcinnamic aldehyde, Georgywood™, hydroxycitronellal, Iso E Super®, Isoraldeine® (methylionone), Hedion®, maltol, methyl cedryl ketone, and vanillin.

ethers and acetals, e.g. Ambrox®, geranyl methyl ether, rose oxide or Spirambrene®.

esters and lactones, e.g. benzyl acetate, cedryl actetate, γ-decalactone, Helvetolide®, γ-undecalactone, vetivenyl acetate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate and geranyl acetate.

macrocycles, e.g. ambrettolide, ethylene brassylate or Exaltolide®.

heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 30 weight percent, more preferably between 5 and 20 weight percent. However, these values are given only by way of example, since the experienced perfumer may also achieve effects or may create novel accords with lower or higher concentrations, e.g. up to about 50 weight percent based on the fragrance composition.

The compounds of the present invention may be employed into the fragrance application simply by directly mixing the fragrance composition with the fragrance application, or they may, in an earlier step be entrapped with an entrapment material such as for example polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation therein of a compound of formula (I) as a fragrance ingredient, either by directly admixing the compound to the application or by admixing a fragrance composition comprising a compound of formula (I), which may then be mixed to a fragrance application, using conventional techniques and methods. Through the addition of an olfactory acceptable amount of a compound of the present invention, the odor notes of a fragrance application will be improved, enhanced or modified.

Thus, the invention furthermore provides a method for improving, enhancing or modifying a fragrance application through the addition thereto of an olfactory acceptable amount of a compound of formula (I).

As used herein, "fragrance application" means any products, such as fine fragrances, e.g. eaux de perfume and eaux de toilette; household products, e.g. detergents for dishwasher, surface cleaner; laundry products, e.g. softener, bleach, detergent; body care products, e.g. shampoo, shower gel; and cosmetics, e.g. deodorants, vanishing cremes, comprising an odorant. This list of products is given by way of illustration and is not to be regarded as being in any way limiting.

Compounds of formula (I) may be prepared by condensation of substituted benzyl cyanides of formula A with the corresponding cycloalkanones of formula B, as depicted below under conditions well known in the art. R, R' and n have the same meaning as given for the compounds of formula (I) above.

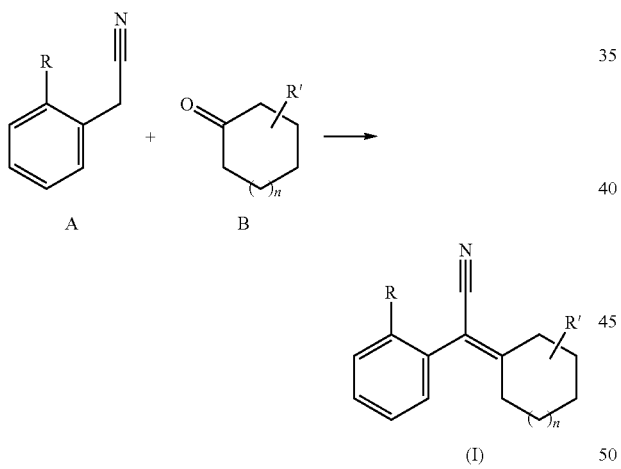

The invention is now further described with reference to the following non-limiting examples.

EXAMPLE 1

Cyclohexylidene-o-tolyl-acetonitrile

The mixture of cyclohexanone (44.7 g, 0.46 mol) and 2-methyl benzylcyanide (41.9 g, 0.32 mol) is treated with KOH (3.58 g, 0064 mol) and the resulting mixture is heated to 120° C. (oilbath temperature 140° C.) for 2 h with concomitant distillation of $H_2O$ as an azeotrope with cyclohexanone. The temperature is raised to 130° C. (oilbath temperature 150° C.) for 30 min, before cooling to 60° C. and dilution of the viscous mixture with toluene (50 ml). Standard aqueous workup is effected with toluene, $H_2O$, sat. aq. $Na_2CO_3$-solution and brine. The organic layer is dried over $MgSO_4$ and the volatiles removed in vacuo. The crude product (67 g), which crystallizes upon standing, is subjected to a short path distillation at 0.05 mbar/120-127° C. to yield 42.6 g of crystalline product which is recrystallized three times from hexane. From this, 33.6 g of white crystalline product is obtained (50% yield), m.p. 65.2-66.0° C.

Odour description: fruity, rosy, Lychee, Palmarosa, Rosacetol.

$^{13}$C-NMR (100 MHz, $CDCl_3$): 162.6 (s), 136.9 (s), 133.01 (s), 130.4 (d), 129.9 (d), 128.6 (d), 126.1 (d), 117.9 (s), 106.5 (s), 34.6 (t), 31.3 (t), 28.1 (t), 27.7 (t), 25.9 (t), 19.6 (q). MS: 211 (64, [M$^+$]), 196 (20), 182 (17), 168 (31), 154 (45), 144 (63), 143 (100).

EXAMPLE 2

Cyclohexylidene-p-tolyl-acetonitrile

The procedure outlined in example 1 is repeated with cyclohexanone (22.34 g, 0.29 mol), p-tolylacetonitrile (20.96 g, 0.16 mol) and KOH (1.79 g, 0.032 mol). Short path distillation of the crude at 0.05 mbar/115-130° C. followed by recrystallization from hexane yields 21.1 g (63% yield) of product as white crystals, m.p. 50.5-51.3° C.

Odour description: floral, rosy, sweet, vanilla $^{13}$C-NMR (100 MHz, $CDCl_3$): 161.3 (s), 138.0 (s), 130.9 (s), 129.2 (d), 129.0 (d), 118.7 (s), 107.5 (s), 35.2 (t), 31.2 (t), 28.0 (t), 27.8 (t), 25.8 (t), 21.1 (q). MS: 211 (21, [M$^+$]), 196 (5), 182 (3), 168 (9), 154 (17), 143 (100).

EXAMPLE 3

Cyclopentylidene-o-tolyl-acetonitrile

The procedure outlined in example 1 is repeated with cyclopentanone (14.3 g, 0.17 mol), o-tolylacetonitrile (13.1 g, 0.10 mol) and KOH (1.12 g, 0.02 mol). Short path distillation of the crude at 0.05 mbar/124-130° C. yields 5.30 g (27% yield). The product is contaminated with α,α'-dicyclopentylidenecyclopentanone. It is further purified by FC on $SiO_2$ to yield 2.3 g of oily product (10% yield).

Odour description: floral, citrus $^{13}$C-NMR (100 MHz, $CDCl_3$): 168.7 (s), 136.2 (s), 133.6 (s), 130.4 (d), 129.3 (d), 128.5 (d), 126.1 (d), 118.0 (s), 105.7 (s), 34.3 (t), 32.8 (t), 26.3 (t), 25.8 (t), 19.5 (q). MS: 197 (82, [M$^+$]), 182 (21), 168 (35), 156 (100), 141 (22), 129 (52), 115 (32).

EXAMPLE 4

Cyclohexylidene-m-tolyl-acetonitrile

Sodium methylate (5.40 g, 0.10 mol) is dissolved in ethanol (70 ml) and 3-methyl benzylcyanide (1310 g, 0.10 mol) is added over 2 min. Cyclohexanone (9.80 g, 0.10 mol) is added to the white suspension. The resulting mixture is heated to 85° C. (bath) for 4.5 h. Under icecooling, formic acid (5.0 ml) is added dropwise, upon which the mixture turns colourless. Standard aqueous workup as described in example 1, followed by a short path distillation at 0.05 mbar/157-165° C. yields 12.2 g of product (58% yield), which is further purified by a fine distillation at 0.05 mbar/183° C. to yield 3.95 g (19%) of product as a colourless oil.

Odour description: floral, citrus $^{13}$C-NMR (100 MHz, $CDCl_3$): 161.7 (s), 138.4 (s), 133.8 (s), 129.8 (d), 128.9 (d), 128.5 (d), 126.3 (d), 118.8 (s), 107.8 (s), 35.4 (t), 31.3 (t), 28.1 (t), 27.9 (t), 25.9 (t), 21.4 (q). MS: 211 (32, [M$^+$]), 196 (8), 182 (7), 168 (18), 154 (25), 143 (100).

EXAMPLE 5

Cyclohexylidene-(2-methoxy-phenyl)-acetonitrile

Sodium methylate (5.40 g, 0.10 mol) is dissolved in ethanol (70 ml) and 2-methoxy benzylcyanide (14.70 g, 0.10 mol) is added over 2 min. Cyclohexanone (9.80 g, 0.10 mol) is added to the white suspension. The resulting mixture is heated to 85° C. (bath) for 4.5 h. Under icecooling, formic acid (5.0 ml) is added dropwise, upon which the mixture turns colourless. Standard aqueous workup as described in example 1, followed by a short path distillation at 0.05 mbar/137-146° C. yields 8.28 g of product (37% yield) as a viscous oil, from which a crystalline byproduct is separated via crystallization from hexane. The mother liquor is concentrated and the residue subjected to a fine distillation at 0.05 mbar/136° C. to yield the product as colourless oil (1.81 g, 8%).

Odour description: floral, rosy, sweet, citronellol.

$^{13}$C-NMR (100 MHz, CDCl$_3$): 162.4 (s), 156.9 (s), 131.0 (d), 129.9 (d), 122.4 (s), 120.4 (d), 118.2 (s), 111.1 (d), 103.5 (s), 55.5 (q), 34.6 (t), 31.5 (t), 27.9 (t), 27.5 (t), 25.8 (t). MS: 227 (99, [M$^+$]), 212 (8), 200 (9), 196 (45), 184 (30), 169 (21), 159 (94), 147 (44), 144 (100).

EXAMPLE 6

(E/Z)-2-(2-methylcyclohexylidene)-2-o-tolylacetonitrile

To the stirred mixture of 2-methylcyclohexanone (12.3 g, 0.11 mol) and o-methyl benzyl cyanide (13.1 g, 0.10 mol) is added sodium methoxide (30% in MeOH, 18.5 ml, 0.10 mol) during 15 min and the resulting brown mixture is heated under stirring to 60° C. (oilbath) for 3 h and 80° C. for further 10 h. The mixture is diluted with toluene, the organic layer washed with brine/H$_2$O 1:1 and dried over MgSO$_4$. The solvent is removed under reduced pressure and the residue distilled over a short-path apparatus at 0.05 mbar. The fraction distilling at 96-124° C. is collected (5.4 g) and further purified by flash chromatography on SiO$_2$, eluting with cyclohexane/methyl-t-butyl ether 9:1. After removal of the solvent, the residue is bulb-to-bulb distilled at 175° C. (0.05 mbar) to yield 2.19 g (9%) of colourless oil, which consists of E/Z-isomers (not attributed) in a 54:46 ratio (GC). The NMR-spectra indicates also the presence of distinguishable rotamers (atropisomers) at room temperature.

Odour description: balsamic, sweet, cinnamic, plum.

$^{13}$C-NMR (100 MHz, CDCl$_3$) (E/Z-mixture and atropisomers at room temperature): 166.6, 166.4, 166.3 (s), 136.7, 136.6 (s), 133.1, 133.0 (s), 130.4, 130.3, 130.3 (d), 130.0, 129.8, 129.6, 129.3 (d), 128.6, 128.5 (d), 126.1, 126.0 (d), 117.7, 117.7, 117.6, 117.5 (s), 106.2, 106.1, 105.9 (s), 36.2, 36.1 (d), 33.2, 33.1 (t), 32.7, 32.3 (d), 29.8, 29.8 (t), 28.3, 28.2 (t), 27.4 (t), 26.8, 26.2 (t), 20.0, 20.0,19.9, 19.9 (t), 19.5, 19.5 (q), 19.2 (q), 18.6, 18.5 (q), 18.1, 17.4 (q). MS (main isomer): 25 (100, [M$^+$]), 210 (86), 196 (26), 182 (40), 168 (57), 154 (70).

EXAMPLE 7

The following compounds may also be prepared according to the general procedure as described in example 1: cyclohexylidene-(2-ethyl-phenyl)-acetonitrile and cyclohexylidene-(2-isopropyl-phenyl)-acetonitrile.

EXAMPLE 8

Determination of GC-odor Threshold Values

According to standard procedures known to the person skilled in the art, threshold values for volatile perfumery compounds are determined on a gas chromatograph equipped with a sniff port by a panel of trained evaluators. The lowest concentration smelled by each panellist is recorded as the individual threshold value expressed in ng (absolute amount of compound delivered at the sniff port).

Under identical conditions the odour threshold value for the individual compounds was measured. The results are given below.

| Compound | Number of panelists | odour threshold value [ng] geometric mean |
|---|---|---|
| Peonile ® | 8 | 0.53 |
| Cyclohexylidene-p-tolyl-acetonitrile | 5 | 2.91 |
| Cyclohexylidene-m-tolyl-acetonitrile | 5 | 1.08 |
| Cyclohexylidene-o-tolyl-acetonitrile | 8 | 0.12 |

It can be seen from the results that the compounds of the present invention have an odour threshold value which is more than 4 times lower compared to the un-substituted compound of the prior art and up to 24 times lower compared to the para- or meta-substituted compound. Based on this, a significant advance is achieved because much smaller amounts of the claimed compounds is required to impart the same odour intensity.

EXAMPLE 9

A Floral-fruity Fragrance Composition for a Powder Detergent

| | Parts per weight |
|---|---|
| Amberketal (3,8,811a-Tetramethyldodecahydro-5H-3,5-a-epoxy-napht(2,1-c)oxepin) | 2 |
| Ambrettolide (Oxacycloheptadec-10-en-2-one) | 5 |
| β-Dihydro ionone (4-(2,6,6-Trimethyl-1-cyclohexen-1-yl)butan-2-one) | 5 |
| Bergamot Givco 104* | 20 |
| Cis-3-Hexenyl salicylate | 35 |
| Citronellol | 25 |
| Cosmone ((Z)-3-Methyl-cyclotetradec-5-en-1-one) | 1 |
| Dihydromyrcenol | 50 |
| Dimethyl benzyl carbinol acetate | 50 |
| Ethyl vanilline | 1 |
| Eugenol | 8 |
| Florhydral (3-(3-Isopropylphenyl)butanal) | 10 |
| Floridile (9-Undecenenitrile) | 1 |
| Freskomenthe (2-sec-Butylcyclohexanone) | 13 |
| Georgywood (cis-1-(1,2,3,4,5,6,7,8-Octahydro-1,2,8,8-tetramethyl-2-naphthalenyl)-ethanone) | 10 |
| Geraniol | 25 |
| Geranyl acetate | 24 |
| Givescone ® (mixture of Methyl 2-ethyl-6,6-dimethyl-cyclohex-2-enecarboxylate and Methyl 2,3,6,6-tetramethylcyclohex-2-enecarboxylate) | 50 |
| Heliotropin | 5 |
| Indolene (8,8-Di-(1H-Indol-1-yl)-2,6-dimethyloctane-2-ol) | 3 |
| Isoeugenol | 3 |
| Javanol ® (1-Methyl-2-(1,2,2-trimethylbicyclo[3.1.0]hex-3-ylmethyl)cyclopropyl)methanol) | 5 |
| Lierral (6-Methyl-8-(1-methylethyl)-bicyclo[2.2.2]oct-5-ene-2-carboxaldehyde) | 0.2 |
| Litsea Cubeba. Ess. | 5 |
| Methyl Pamplemousse (1,1-Dimethoxy-2,2,5-trimethyl-4-hexene) | 5 |
| 2-Methylundecanal | 5 |
| Peonile ® | 100 |
| Phenylethanol | 250 |
| Pomarose ((2E)-5,6,7-Trimethyl-2,5-octadien-4-one) | 3 |

-continued

| | Parts per weight |
|---|---|
| Silvial (2-Methyl-3-(4-(2-methylpropyl)phenyl)-propanal) | 80 |
| Spirogalbanone (1-Spiro[4.5]dec-7-en-7-yl-4-penten-1-one) in 10% DPG** | 5.8 |
| Stemone ® (5-Methyl-3-heptanone oxime) | 5 |
| Super Muguet (6-Ethyl-3-methyl-6-octen-1-ol) | 20 |
| Tetrahydro Linalool | 105 |
| Tricyclal (2,4-Dimethyl-3-cyclohexene-1-carboxaldehyde) | 10 |
| Undecavertol (4-Methyl-dec-3-en-5-ol) | 30 |
| Ylang Ylang Ess. | 25 |
| | 1000 |

*Supplier: Givaudan SA (Fragrance Ingredients Index 2004)
**DPG is understood to mean dipropylene glycol Replacing 100 parts of Peonile® by cyclohexylidene-o-tolyl-acetonitrile enhances the floral rosy aspect of the fragrance, adds notes of exotic fruits such as Lychee and makes the composition much more elegant.

The invention claimed is:

1. A compound of formula (I)

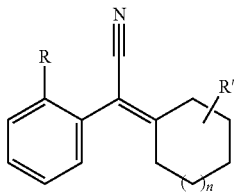

(I)

wherein

R is selected from methyl, ethyl, propyl, isopropyl, methoxy and ethoxy;

R' is hydrogen or methyl; and n is 0 or 1.

2. A compound according to claim 1 selected from the group consisting of:
cyclohexylidene-o-tolyl-acetonitrile,
cyclopentylidene-o-tolyl-acetonitrile,
cyclohexylidene-(2-methoxy-phenyl)-acetonitrile,
2-(2-methylcyclohexylidene)-2-o-tolylacetonitrile,
cyclohexylidene-(2-ethyl-phenyl)-acetonitrile, and,
cyclohexylidene-(2-isopropyl-phenyl)-acetonitrile.

3. An odorant composition which comprises a compound of formula (I) as defined in claim 1.

4. A fragrance composition comprising a compound of formula (I) as defined in claim 1.

5. A method of manufacturing a fragrance composition, comprising the step of incorporation a compound of formula (I) as defined in claim 1 into a base material.

6. A method of manufacturing a fragrance application, comprising the incorporation of a compound of formula (I) as defined in claim 1.

7. A method of improving, enhancing or modifying a fragrance application through the addition of an olfactory acceptable amount of a compound of formula (I) as defined in claim 1.

8. A method according to claim 6 wherein the fragrance application is selected from the group consisting of perfumes, household products, laundry products, body care products and cosmetics.

9. An odorant composition which comprises a compound of formula (I) as defined in claim 2.

10. A fragrance composition comprising a compound of formula (I) as defined in claim 2.

11. A method of manufacturing a fragrance composition, comprising the step of incorporation a compound of formula (I) as defined in claim 2 into a base material.

12. A method of manufacturing a fragrance application, comprising the incorporation of a compound of formula (I) as defined in claim 2.

13. A method of improving, enhancing or modifying a fragrance application through the addition of an olfactory acceptable amount of a compound of formula (I) as defined in claim 1.

14. A method according to claim 13 wherein the fragrance application is selected from the group consisting of perfumes, household products, laundry products, body care products and cosmetics.

* * * * *